United States Patent
Parthasaradhi Reddy et al.

(10) Patent No.: US 9,624,172 B2
(45) Date of Patent: Apr. 18, 2017

(54) POLYMORPHS OF LOMITAPIDE AND ITS SALTS

(71) Applicant: Hetero Research Foundation, Hyderabad,Andhra Pradesh (IN)

(72) Inventors: Bandi Parthasaradhi Reddy, Hyderbad (IN); Kura Rathnakar Reddy, Andhra Paresh (IN); Dasari Muralidhara Reddy, Hyderabad (IN); Jambula Mukunda Reddy, Hyderabad (IN); Bandi Vamsi Krishna, Hyderabad (IN)

(73) Assignee: Hetero Research Foundation, Balanagar, Hyderabad (IN)

( * ) Notice: Subject to any disclaimer, the term of this patent is extended or adjusted under 35 U.S.C. 154(b) by 0 days.

(21) Appl. No.: 15/119,294

(22) PCT Filed: Feb. 13, 2015

(86) PCT No.: PCT/IN2015/000087
§ 371 (c)(1),
(2) Date: Aug. 16, 2016

(87) PCT Pub. No.: WO2015/121877
PCT Pub. Date: Aug. 20, 2015

(65) Prior Publication Data
US 2017/0057917 A1  Mar. 2, 2017

(30) Foreign Application Priority Data
Feb. 17, 2014  (IN) .............................. 723/CHE/2014

(51) Int. Cl.
*C07D 211/58*  (2006.01)

(52) U.S. Cl.
CPC .................................. *C07D 211/58* (2013.01)

(58) Field of Classification Search
None
See application file for complete search history.

(56) References Cited

U.S. PATENT DOCUMENTS

| | | | |
|---|---|---|---|
| 5,712,279 A | 1/1998 | Biller et al. | |
| 5,883,109 A * | 3/1999 | Gregg .................... | A61K 45/06 514/321 |
| 6,949,572 B2 | 9/2005 | Bertinato et al. | |
| 7,468,378 B2 | 12/2008 | Bertinato et al. | |
| 2012/0296091 A1 | 11/2012 | Sieger et al. | |

FOREIGN PATENT DOCUMENTS

WO  WO 2015/077154 A1  5/2015

OTHER PUBLICATIONS

Goldberg et al., Emerging low density lipoprotein therapies: Microsomal triglyceride transfer protein inhibitors, Journal of Clinical Lipidology, 7:S16-S20, 2013.
Zhang et al., Crystal structure of 9-(4-bromobutyl)-9H-fluorene-9-carboxylic acid, Acta Cryst., E70:o1118-o1119, 2014.

* cited by examiner

*Primary Examiner* — Timothy R Rozof
(74) *Attorney, Agent, or Firm* — John D. Thallemer

(57) ABSTRACT

The present invention provides novel polymorphs of Lomitapide, process for their preparation and pharmaceutical compositions comprising them. The present invention also provides a novel polymorph of Lomitapide mesylate, process for its preparation and pharmaceutical compositions comprising it.

16 Claims, 3 Drawing Sheets

POLYMORPHS OF LOMITAPIDE AND ITS SALTS

FIELD OF THE INVENTION

The present invention provides novel polymorphs of Crystalline Lomitapide and a novel amorphous form of Lomitapide mesylate, process for their preparation and pharmaceutical compositions comprising them.

BACKGROUND OF THE INVENTION

Lomitapide mesylate is a drug for the treatment of hyperchloesterolemia. It has been tested in clinical trials as single treatment and in combinations with atorvastatin, ezetimibe and fenofibrate. The generic name Lomitapide mesylate is marketed by AEGERION under the brand name Juxtapid®.

Lomitapide is chemically, N-(2,2,2-trifluoroethyl)-9-[4-[4-[[[4'-(trifluoromethyl)[1,1'-biphenyl]-2-yl]carbonyl]amino]-1-piperidinyl]-butyl-9H-fluorene-9-carboxamide and has the structural formula:

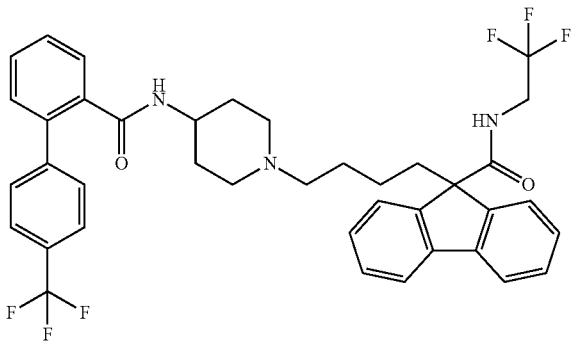 [SMILES: O=C(NC1CCN(CCCCC2(C(=O)NCC(F)(F)F)c3ccccc3-c3ccccc32)CC1)c1ccccc1-c1ccc(C(F)(F)F)cc1]

Lomitapide and its mesylate salt were disclosed in U.S. Pat. No. 5,712,279.

Polymorphism is defined as "the ability of a substance to exist as two or more crystalline phases that have different arrangement and/or conformations of the molecules in the crystal Lattice. Thus, in the strict sense, polymorphs are different crystalline structures of the same pure substance in which the molecules have different arrangements and/or different configurations of the molecules". Different polymorphs may differ in their physical properties such as melting point, solubility, X-ray diffraction patterns, etc. Although those differences disappear once the compound is dissolved, they can appreciably influence pharmaceutically relevant properties of the solid form, such as handling properties, dissolution rate and stability. Such properties can significantly influence the processing, shelf life, and commercial acceptance of a polymorph. It is therefore important to investigate all solid forms of a drug, including all polymorphic forms, and to determine the stability, dissolution and flow properties of each polymorphic form. Polymorphic forms of a compound can be distinguished in the laboratory by analytical methods such as X-ray diffraction (XRD). Differential Scanning Calorimetry (DSC) and Infrared spectrometry (IR).

Solvent medium and mode of crystallization play very important role in obtaining one polymorphic Form over the other.

Lomitapide and its mesylate salt can exist in different polymorphic Forms, which may differ from each other in terms of stability, physical properties, spectral data and methods of preparation.

We have found two novel polymorphs of Lomitapide. The polymorphs of Lomitapide are stable, reproducible and so, the polymorph of Lomitapide is suitable for pharmaceutical preparations.

The novel polymorphs of Lomitapide are useful intermediate for the preparation of Lomitapide mesylate.

We have also found a novel polymorph of Lomitapide mesylate. The polymorph of Lomitapide mesylate is stable, reproducible and so, the polymorph of Lomitapide mesylate is suitable for pharmaceutical preparations.

Objectives

One objective of the present invention is to provide novel crystalline Forms of Lomitapide, which are stable, reproducible and suitable for pharmaceutical compositions.

Another objective of the present invention is to provide novel amorphous Form of Lomitapide mesylate, which is stable, reproducible and suitable for pharmaceutical compositions.

Another objective of the present invention is to provide the novel amorphous Form of Lomitapide mesylate having high purity greater than 97% by using novel crystalline Forms of Lomitapide of this present invention.

SUMMARY OF THE INVENTION

In one aspect, the present invention provides a crystalline Form of Lomitapide designated as Form 1 characterized by peaks iii the powder x-ray diffraction spectrum having 2θ angle positions at about 7.7, 15.5, 17.3, 20.2, 21.4 and 21.9±0.2 degrees.

In another aspect, the present invention provides a process for the preparation of Lomitapide crystalline Form 1, which comprises:
a) suspending Lomitapide in a hydrocarbon solvent;
b) heating the contents obtained in step (a) above 50° C.;
c) adding a ketonic solvent to the solution;
d) adding a hydrocarbon solvent to the solution; and
e) isolating Lomitapide crystalline Form 1.

In another aspect, the present invention provides a pharmaceutical composition comprising crystalline Form 1 of Lomitapide and pharmaceutically acceptable excipients.

In another aspect, the present invention provides a crystalline Form of Lomitapide designated as Form 2 characterized by peaks in the powder x-ray diffraction spectrum having 2θ angle positions at about 5.5, 10.9, 13.5, 13.7, 18.2, 19.0 and 22.0±0.2 degrees.

In another aspect, the present invention provides a process for the preparation of Lomitapide crystalline Form 2, which comprises:
a) suspending Lomitapide in a solvent;
b) heating the contents obtained in step (a) at 75 to 85° C.;
c) maintain for 30 minutes and then cooled to room temperature; and
d) isolating Lomitapide crystalline Form 2.

In another aspect, the present invention provides a pharmaceutical composition comprising crystalline Form 2 of Lomitapide and pharmaceutically acceptable excipients.

In another aspect, the present invention provides an amorphous Lomitapide mesylate.

In another aspect, the present invention provides a process for the preparation of amorphous Lomitapide mesylate, which comprises:
a) dissolving Lomitapide in an alcoholic solvent;
b) adding methanesulfonic acid to the solution obtained in step (a);
c) adding a hydrocarbon solvent to the contents;

d) removing the solvents from the solution to obtain a residual solid;
e) adding a hydrocarbon solvent to the residual solid obtained in step (d); and
f) isolating amorphous Lomitapide mesylate.

Yet in another aspect, the present invention provides pharmaceutical compositions comprising a therapeutically effective amount of amorphous Lomitapide mesylate and at least one pharmaceutically acceptable excipient.

Powder X-ray diffraction spectrum was measured on a bruker AXS D8 advance powder X-ray diffractometer having a copper-Kα radiation. Approximately 500 mg of sample was gently flattered on a sample holder and scanned from 2 to 50 degrees two-theta, at 0.020 degrees two theta per step and a step time of 1 second. The sample was simply placed on the sample holder. The sample was rotated at 30 rpm at a voltage 40 kV and current 35 mA.

DETAILED DESCRIPTION OF THE INVENTION

The term "room temperature" refers to temperature at about 25 to 35° C.

Figure 1:
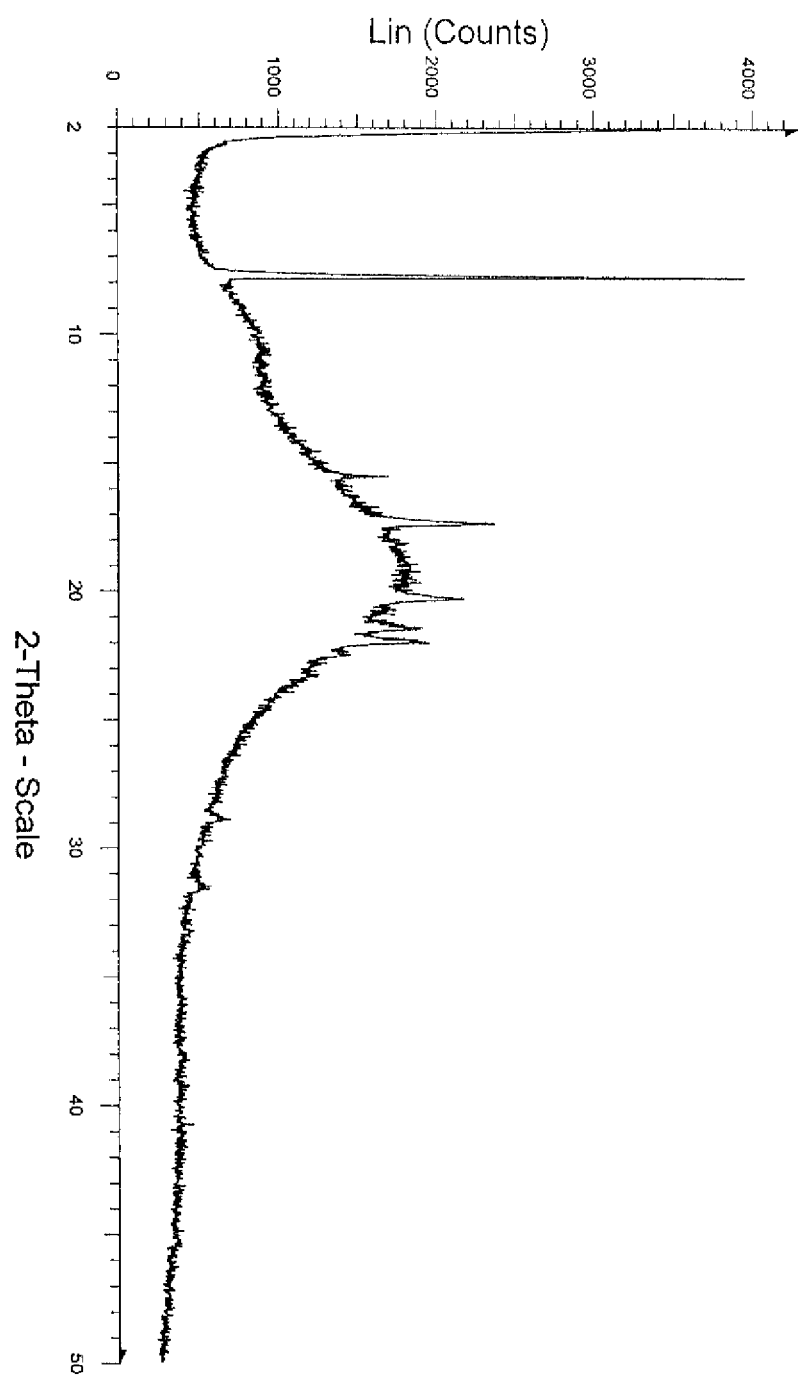
FIG. 1 is a powder X-ray diffractogram patterns of Lomitapide crystalline Form 1.

According to one aspect of the present invention, there is provided a crystalline Form of Lomitapide designated as Form 1 characterized by peaks in the powder x-ray diffraction spectrum having 2θ angle positions at about 7.7, 15.5, 17.3, 20.2, 21.4 and 21.9±0.2 degrees. The powdered x-ray diffractogram (PXRD) of Lomitapide crystalline Form 1 is shown in FIG. 1.

According to another aspect of the present invention, there is provided a process for the preparation of Lomitapide crystalline Form 1, which comprises:
a) suspending Lomitapide in a hydrocarbon solvent;
b) heating the contents obtained in step (a) above 50° C.;
c) adding a ketonic solvent to the solution;
d) adding a hydrocarbon solvent to the solution; and
e) isolating Lomitapide crystalline Form 1.

Lomitapide used in step (a) may preferably be Lomitapide obtained by the known process.

The hydrocarbon solvent used in step (a) and (d) may preferably be a solvent or a mixture of solvents selected from cyclohexane, hexane, heptane, n-hexane, n-heptane, toluene and xylene. More preferably the hydrocarbon solvents are n-hexane and toluene.

Step (b) may preferably be carried out at about 55 to 80° C. and more preferably at about 60 to 75° C.

The ketonic solvent used in step (c) may preferably be a solvent or a mixture of solvents selected from acetone, methyl ethyl ketone, diethyl ketone and methyl isobutyl ketone. More preferably the ketonic solvent is acetone.

The step (e) may conveniently be carried out at room temperature.

Isolation of Lomitapide crystalline Form 1 in step (e) can be performed by conventional methods such as cooling, removal of solvents, concentrating the reaction mass, adding an anti-solvent, extraction with a solvent, filtration, centrifugation and the like.

According to another aspect of the present invention, there is provided a pharmaceutical composition comprising crystalline Form 1 of Lomitapide and pharmaceutically acceptable excipients, and optionally other therapeutic ingredients. The crystalline Form 1 may preferably be formulated into tablets, capsules, suspensions, dispersions, injectables or other pharmaceutical forms.

Figure 2:
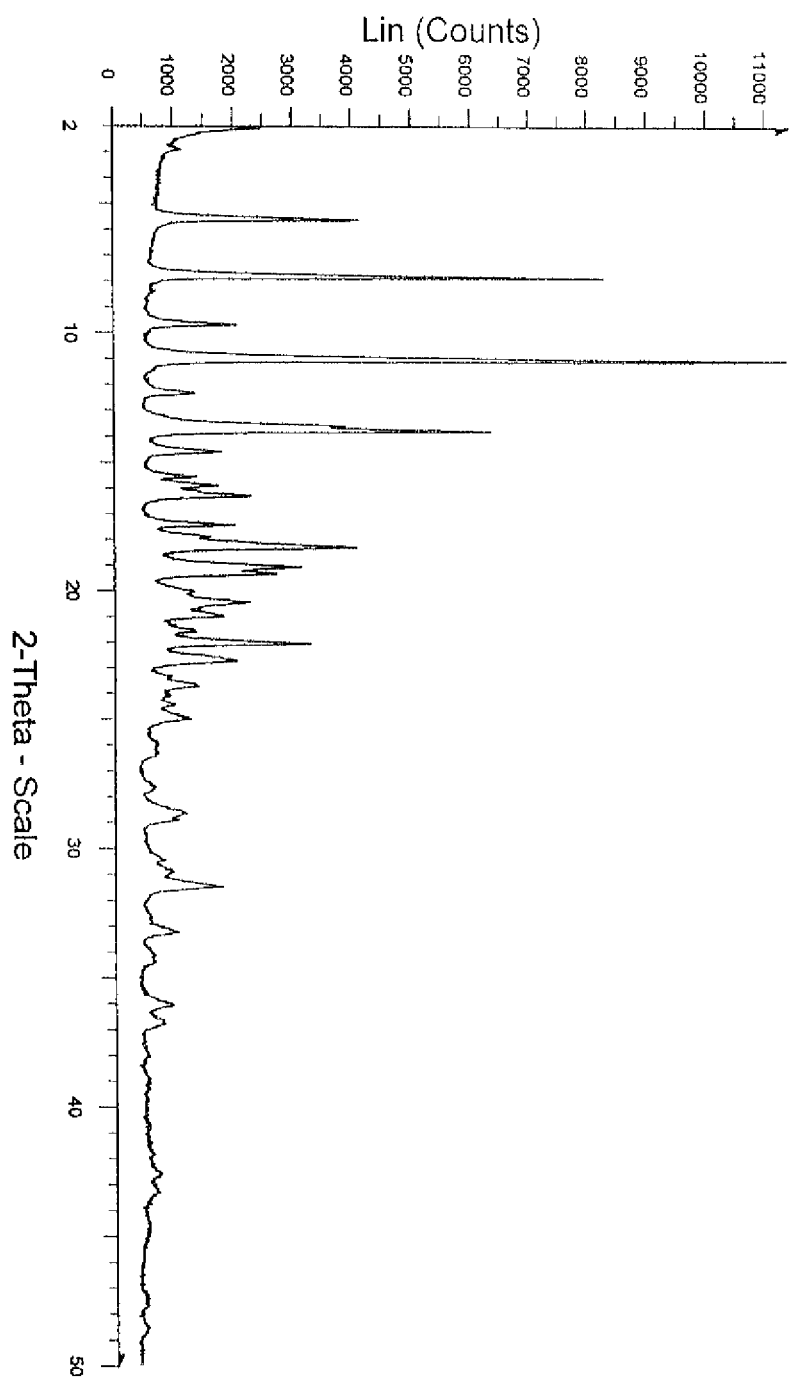
FIG. 2 is a powder X-ray diffractogram patterns of Lomitapide crystalline Form 2.

According to another aspect of the present invention, there is provided a crystalline Form of Lomitapide designated as Form 2 characterized by peaks in the powder x-ray diffraction spectrum having 2θ angle positions at about 5.5, 10.9, 13.5, 13.7, 18.2, 19.0 and 22.0±0.2 degrees. The powdered x-ray diffractogram (PXRD) of Lomitapide crystalline Form 2 is shown in FIG. 2.

According to another aspect of the present invention, there is provided a process for the preparation of Lomitapide crystalline Form 2, which comprises:
a) suspending Lomitapide in a solvent;
b) heating the contents obtained in step (a) at 75 to 85° C.;
c) maintain for 30 minutes and then cooled to room temperature; and
d) isolating Lomitapide crystalline Form 2.

Lomitapide used in step (a) may preferably be Lomitapide obtained by the known process.

The solvent used in step (a) may preferably be a solvent or a mixture of solvents selected from acetonitrile, propionitrile, cyclohexane, hexane, heptane, n-hexane, n-heptane, toluene, xylene, acetone, methyl ethyl ketone, diethyl ketone, methyl isobutyl ketone, methanol, ethanol, isopropyl alcohol, tert-butyl alcohol, n-butanol, isobutyl alcohol, tetrahydrofuran, diisopropyl ether, 1,4-dioxane and dimethyl formamide. More preferably the solvent is selected from acetonitrile, methanol, toluene, tert-butyl alcohol and dimethyl formamide.

Isolation of Lomitapide crystalline Form 2 in step (d) can be performed by conventional methods such as cooling, removal of solvents, concentrating the reaction mass, adding an anti-solvent, extraction with a solvent, filtration, centrifugation and the like.

According to another aspect of the present invention, there is provided a pharmaceutical composition comprising crystalline Form 2 of Lomitapide and pharmaceutically acceptable excipients, and optionally other therapeutic ingredients. The crystalline Form 2 may preferably be formulated into tablets, capsules, suspensions, dispersions, injectables or other pharmaceutical forms.

Figure 3:
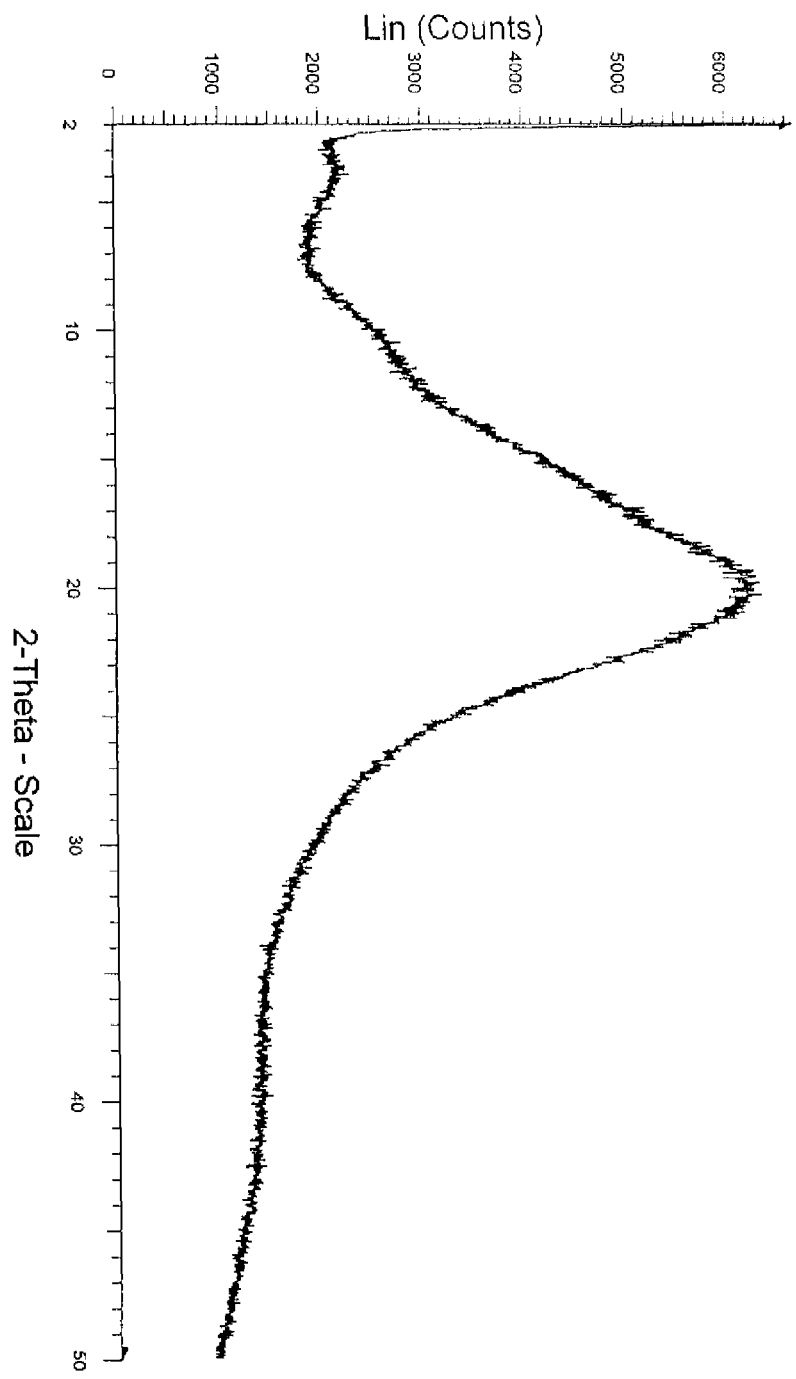
FIG. 3 is a powder X-ray diffractogram patterns of amorphous Lomitapide mesylate.

According to another aspect of the present invention, there is provided an amorphous Lomitapide mesylate. The powdered x-ray diffractogram (PXRD) of amorphous Lomitapide mesylate is shown in FIG. 3.

Normally amorphous Forms are hygroscopic. Amorphous Lomitapide mesylate is found to be non-hygroscopic.

According to another aspect of the present invention, there is provided a process for the preparation of amorphous Lomitapide mesylate, which comprises:
a) dissolving Lomitapide in alcoholic solvent;
b) adding methanesulfonic acid to the solution obtained in step (a);
c) adding a hydrocarbon solvent to the contents;
d) removing the solvents from the solution to obtain a residual solid;
e) adding a hydrocarbon solvent to the residual solid obtained in step (d); and
f) isolating amorphous Lomitapide mesylate.

Lomitapide used in step (a) may preferably be Lomitapide obtained by the known process or Lomitapide crystalline Form 1 or Form 2.

The alcoholic solvent used in step (a) may preferably be a solvent or a mixture of solvents selected from methanol, ethanol, isopropyl alcohol, tert-butyl alcohol, n-butanol and isobutyl alcohol. More preferably the alcoholic solvent is isopropyl alcohol.

The hydrocarbon solvent used in step (c) and (e) may preferably be a solvent or a mixture of solvents selected from cyclohexane, hexane, heptane, n-hexane, n-heptane, toluene and xylene. More preferably the hydrocarbon solvent is heptane.

The solvents may be removed from the solution in step (d) by known methods, for example, distillation or spray drying.

The distillation of the solvent may be carried out at atmospheric pressure or at reduced pressure. The distillation may preferably be carried out until the solvent is almost completely distilled off.

As used herein, "reduced pressure" refers to a pressure of less than 100 mmHg.

The term "Spray drying" refers to is a method of producing a dry powder from a liquid or slurry by rapidly drying with a hot gas.

Isolation of amorphous Lomitapide mesylate may preferably be carried out by methods known such as filtration or centrifugation.

According to another aspect of the present invention, there is provided pharmaceutical compositions comprising a therapeutically effective amount of amorphous Lomitapide mesylate, and at least one pharmaceutically acceptable excipient. The amorphous Lomitapide mesylate may preferably be formulated into tablets, capsules, suspensions, dispersions, injectables or other pharmaceutical forms.

Preferably the present invention provides a pharmaceutical composition containing said solid dispersion along with the pharmaceutically acceptable excipients such as diluents, chelating agents, disintegrant, glidant, binders, surfactants, coloring agents and/or lubricants.

Specific examples of binders include methyl cellulose, hydroxypropyl cellulose, hydroxypropyl methylcellulose, polyvinylpyrrolidone, gelatin, gum Arabic, ethyl cellulose, polyvinyl alcohol, pullulan, pregelatinized starch, agar, tragacanth, sodium alginate, propylene glycol, and the like.

Specific examples of diluents include calcium carbonate, calcium phosphate-dibasic, calcium phosphate-tribasic, calcium sulfate, microcrystalline cellulose, cellulose powdered, dextrates, dextrins, dextrose excipients, fructose, kaolin, lactitol, lactose, mannitol, sorbitol, starch, starch pregelatinized, sucrose, sugar compressible, sugar confectioners, and the like and mixtures thereof.

Surfactants include both non-ionic and ionic (cationic, anionic and zwitterionic) surfactants suitable for use in pharmaceutical dosage forms. These include polyethoxylated fatty acids and its derivatives, for example, polyethylene glycol 400 distearate, polyethylene glycol—20 dioleate, polyethylene glycol 4—150 mono dilaurate, and polyethylene glycol—20 glyceryl stearate; alcohol—oil transesterification products, for example, polyethylene glycol—6 corn oil; polyglycerized fatty acids, for example, polyglyceryl—6 pentaoleate; propylene glycol fatty acid esters, for example, propylene glycol monocaprylate; mono and diglycerides, for example, glyceryl ricinoleate; sterol and sterol derivatives; sorbitan fatty acid esters and its derivatives, for example, polyethylene glycol—20 sorbitan monooleate and sorbitan monolaurate; polyethylene glycol alkyl ether or phenols, for example, polyethylene glycol—20 cetyl ether and polyethylene glycol—10-100 nonyl phenol; sugar esters, for example, sucrose monopalmitate; polyoxyethylene—polyoxypropylene block copolymers known as "poloxamer"; ionic surfactants, for example, sodium caproate, sodium glycocholate, soy lecithin, sodium stearyl fumarate, propylene glycol alginate, octyl sulfosuccinate disodium, and palmitoyl carnitine; and the like and mixtures thereof.

Specific examples of disintegrants include low-substituted hydroxypropylcellulose (L-HPC), sodium starch glycollate, carboxymethyl cellulose, calcium carboxymethyl cellulose, sodium carboxymethyl cellulose, croscarmellose sodium A-type (Ac-di-sol), starch, crystalline cellulose, hydroxypropyl starch, pregelatinized starch, and the like and mixtures thereof.

Specific examples of lubricants/glidants include colloidal silicon dioxide, stearic acid, magnesium stearate, calcium stearate, talc, hydrogenated castor oil, sucrose esters of fatty acid, microcrystalline wax, yellow beeswax, white beeswax, and the like and mixtures thereof.

Coloring agents include any FDA approved colors for oral use.

The invention will now be further described by the following examples, which are illustrative rather than limiting.

EXAMPLES

Example 1

Preparation of N-(piperidin-4-yl)-4'-(trifluoromethyl)-[1,1-biphenyl]-2-carboxamide 4'-(Trifluoromethyl)-[1,1'-biphenyl]-2-carboxylic acid (10 gm) was dissolved in toluene (50 ml) and added hydroxybenzotriazole (6.1 gm) at room temperature. The mixture was cooled to −10 to −15° C. and a solution of N,N'-Dicyclohexylcarbodiimide (12 gm) in toluene (60 ml) was added to the mixture slowly for 45 minutes. The temperature of the reaction mass was raised to room temperature and filtered. The filtrate thus obtained was added to a mixture of 4-amino-1-benzylpiperidine (6 gm) in toluene (20 ml) and triethylamine (47 gm) slowly for 1 hour at room temperature. The reaction mass was cooled to 10 to 15° C. and filtered. The solid obtained was dried to obtain 13 gm of N-(1-benzylpiperidin-4-yl)-4'-(trifluoromethyl)-[1,1'-biphenyl]-2-carboxamide.

N-(1-Benzylpiperidin-4-yl)-4'-(trifluoromethyl)-[1,1'-biphenyl]-2-carboxamide (50 gm) was dissolved in methanol (750 ml) and palladium carbon (10%; 12 gm) in water (100 ml) was then added. The reaction mass was applied hydrogen gas and then heated to 50 to 55° C. The reaction mass was maintained for 3 hours at 50 to 55° C. and cooled to room temperature. The separated solid was filtered and then dried to obtain 60.4 gm of N-(piperidin-4-yl)-4'-(trifluoromethyl)-[1,1'-biphenyl]-2-carboxamide.
Yield: 70%
Chromatographic purity (by HPLC): 97.8%

Example 2

Preparation of 9-(4-broniobutyl)-N-(2,2,2-tritluoroethyl)-9H-fluorene-9-carboxamide Tetrahydrofuran (2400 ml) was added to 9H-fluorene-9-carboxylic acid (100 gm) under stirring, The solution was cooled to 0 to −5° C. and a solution of n-butyllithium (60.9 gm) in n-hexane (340 ml) was then added slowly. The reaction mass was maintained for 1 hour at 0 to −5° C. and 1,4-dibromo butane (133.5 gm) was added to the reaction mass slowly. The reaction mass was maintained for 40 minutes at 0 to −5° C. and temperature of the reaction mass was raised to room temperature. The reaction mass was maintained for 15 hours at room temperature and then cooled to 0 to 5° C. To the reaction mass was added hydrochloric acid solution (1N, 1000 ml) at 0 to −5° C. slowly and temperature of the reaction mass was raised to room temperature. The layers were separated and the aqueous layer was extracted with ethyl acetate. Combined organic layers were dried with sodium sulfate and the solvent was distilled off under vacuum to obtain a residual solid. The residual solid obtained was dissolved in n-hexane (1000 ml) and stirred for 2 hours. The separated solid was filtered and then dried to obtain 98.6 gm of 9-(4-bromobutyl)-9H-fluorene-9-carboxylic acid.

2,2,2-Trifluoroethyl amine (3.1 gm) was dissolved in water (20 ml) and pH was adjusted to 10.5 to 11.0 with sodium hydroxide solution (10%). The solution was extracted three times with methylene chloride. Combined organic layers were dried with sodium sulfate and 9-(4-bromobutyl)-9H-fluorene-9-carboxylic acid was added to the organic layer. The reaction mass was cooled to 0 to 5° C. and a solution of N,N'-dicyclohexylcarbodiimide (11.3 gm) in methylene chloride (60 ml) was then added. The reaction mass was maintained for 2 hours at 0 to 5° C. and the temperature of the reaction mass was raised to room temperature for 30 minutes. The reaction mass was cooled to −5° C., maintained for 30 minutes and filtered to obtain a wet solid. The wet solid was dissolved in n-hexane (30 ml) and cooled to 0 to 5° C. The contents were stirred for 2 hours and filtered. The solid obtained was dried to obtain 8 gm of 9-(4-bromobutyl)-N-(2,2,2-tritluoroethyl)-9H-fluorene-9-carboxamide.
Yield: 64.8%
Chromatographic purity (by HPLC): 90.25%

Example 3

Preparation of Lomitapide 9-(4-Bromobutyl)-N-(2,2,2-trifluoroethyl)-9H-fluorene-9-carboxamide (1 gm) was dissolved in dimethylformamide (10 ml) and potassium carbonate (0.64 gm) and N-(piperidin-4-yl)-4'-(trifluoromnethyl)-[1,1'-biphenyl]-2-carboxamide (0.8 gm) were then added. The reaction mass was heated to 55 to 60° C. and maintained for 75 hours. The reaction mass was cooled to room temperature and water (100 ml) was added to the reaction mass. To the reaction mass was added methylene chloride (50 ml) and stirred for 10 minutes. The layers were separated and the aqueous layer was extracted with methylene chloride. Combined organic layers were dried with sodium sulfate and then concentrated to obtain 2.1 gm of Lomitapide.
Yield: 86%
Chromatographic purity (by HPLC): 93%

Preparation of Lomitapide

N-(piperidin-4-yl)-4'-(trifluoromethyl)-[1,1'-biphenyl]-2-carboxamide hydrochloride (25 gm) was dissolved in dimethylformamide (130 ml) and was added 9-(4-Bromobutyl)-N-(2,2,2-trifluoroethyl)-9H-fluorene-9-carboxamide (30 gm). To the above raction mixture, Triethylamine (20 gm) was added at room temperature. The reaction mass was maintained for 18 hours. Water (800 ml) was added to the reaction mixture and maintained for 6 hours to 7 hours. The obtained crystalline solid was filtered and washed with water (200 ml) and then dried to obtain 34 gm of Lomitapide.
Yield: 75%
Chromatographic purity (by HPLC): 92.58%

Example 4

Preparation of Crystalline Lomitapide Form 1

Lomitapide (10 gm) was dissolved in toluene (40 ml) and heated to 60 to 65° C. To the solution was added acetone (20 ml) at 60 to 65° C. and n-hexane (200 ml) was then added slowly for 40 minutes at 60 to 65° C. The solution was cooled to room temperature and maintained for 18 hours. The separated solid was filtered and then dried to obtain 7.8 gm of Lomitapide crystalline Form 1.
Yield: 78%
Chromatographic purity (by HPLC): 97%

Example 5

Preparation of Crystalline Lomitapide Form 2

Lomitapide (34 gm) was dissolved in Acetonitrile (100 ml) and heated at 81° C. then maintained for 30 minutes. The reaction mass was cooled to room temperature and maintained for 1 hour. The separated solid was filtered and washed with Acetonitrile (25 ml) then dried to obtain 32 gm of Lomitapide crystalline Form 2.
Yield: 96.76%
Chromatographic purity (by HPLC): 94.11%

Lomitapide (32 gm) was dissolved in Acetonitrile (70 ml) and heated at 81° C. then maintained for 30 minutes. The reaction mass was cooled to room temperature and maintained for 1 hour. The separated solid was filtered and washed with Acetonitrile (25 ml) then dried to obtain 31 gm of Lomitapide crystalline Form 2.
Yield: 96%
Chromatographic purity (by HPLC): 99.7%

Example 6

Preparation of Amorphous Lomitapide Mesylate

Lomitapide (2 gm) was dissolved in isopropyl alcohol (10 ml) and methanesulfonic acid (0.27 gm) was then added at room temperature. To the mixture was added heptane (20 ml) and maintained for 1 hour. The solvents were distilled off under vacuum below 45° C. to obtain a residual solid. To the residual solid was added heptane (20 ml) and maintained for 4 hours at room temperature. The separated solid was filtered and then dried to obtain 1.7 gm of amorphous Lomitapide mesylate.
Yield: 75%
Chromatographic purity (by HPLC): 97%

Example 7

Preparation of Amorphous Lomitapide Mesylate

Lomitapide crystalline Form 1 (10 gm) as obtained in example 4 was dissolved in isopropyl alcohol (50 ml) and methanesulfonic acid (1.3 gm) was then added at room temperature. To the mixture was added heptane (100 ml) and maintained for 1 hour. The solvents were distilled off under vacuum below 45° C. to obtain a residual solid. To the residual solid was added heptane (100 ml) and maintained for 4 hours at room temperature. The separated solid was filtered and then dried to obtain 8.6 gm of amorphous Lomitapide mesylate.

Yield: 79%

Chromatographic purity (by HPLC): 97%

Example 8

Preparation of Amorphous Lomitapide Mesylate

Lomitapide crystalline Form 2 (4.5 gm) as obtained in example 5 was dissolved in methanol (20 ml) and the reaction mass was cooled to −5° C. to 5° C. To this reaction mixture methanesulfonic acid (0.5 ml) was then added at −5° C. to 5° C. and maintained for 30 minutes to 45 minutes and then treated with activated carbon (0.75 gm). The reaction mixture was maintained for 30 minutes and filtered the solid and then washing with methanol (25 ml). Distilled at 30 to 40° C. and dried the solid to yield 5 gm of amorphous Lomitapide mesylate.

Yield: 98.23%

Chromatographic purity (by HPLC): 99.85%

We claim:

1. Crystalline Lomitapide, wherein designated as Form I, Form 2.

2. Form I of Crystalline Lomitapide of claim 1, having a Powder X-ray diffractogram as shown in FIG. 1.

3. Form I of Crystalline Lomitapide of claim 1, characterized by peaks in the powder x-ray diffraction spectrum having 2θ angle positions at about 7.7, 15.5, 17.3, 20.2, 21.4 and 21.9±0.2 degrees.

4. The process for the preparation of the Form I of Crystalline Lomitapide of claim 1, which comprises:
 a) suspending Lomitapide in a hydrocarbon solvent;
 b) heating the contents obtained in step (a) above 50° C.;
 c) adding a ketonic solvent to the solution;
 d) adding a hydrocarbon solvent to the solution; and
 e) isolating Lomitapide crystalline Form 1.

5. The process as claimed in claim 4, wherein the hydrocarbon solvent is preferably selected from the group consisting of cyclohexane, hexane, heptane, n-hexane, n-heptane, toluene, xylene or mixture thereof and more preferably heptane.

6. The process as claimed in claim 4, wherein the ketonic solvent is preferably selected from the group consisting of acetone, methyl ethyl ketone, diethyl ketone, methyl isobutyl ketone or mixture thereof and more preferably acetone.

7. Form 2 of Crystalline Lomitapide of claim 1, having a Powder X-ray diffractogram as shown in FIG. 2.

8. Form 2 of Crystalline Lomitapide of claim 1, characterized by peaks in the powder x-ray diffraction spectrum having 2θ angle positions at about 5.5, 10.9, 13.5, 13.7, 18.2, 19.0 and 22.0±0.2 degrees.

9. The process for the preparation of the Form 2 of Crystalline Lomitapide of claim 1, which comprises:
 a) suspending Lomitapide in a solvent;
 b) heating the contents obtained in step (a) at 75 to 85° C.;
 c) maintain for 30 minutes and then cooled to room temperature; and
 d) isolating Lomitapide crystalline Form 2.

10. The process as claimed in claim 9, wherein the solvent is preferably selected from the group consisting of acetonitrile, propionitrile, methanol, isopropyl alcohol, tert-butyl alcohol, toluene, dimethyl formamide or mixture thereof and more preferably acetonitrile.

11. A pharmaceutical composition comprising Form 1 or Form 2 of Crystalline Lomitapide and pharmaceutically acceptable excipients.

12. Amorphous Lomitapide mesylate having a Powder X-ray diffractogram as shown in FIG. 3.

13. The process for the preparation of Amorphous Lomitapide mesylate of claim 12, which comprises:
 a) dissolving Lomitapide in an alcoholic solvent;
 b) adding methanesulfonic acid to the solution obtained in step (a);
 c) adding a hydrocarbon solvent to the contents;
 d) removing the solvents from the solution to obtain a residual solid;
 e) adding a hydrocarbon solvent to the residual solid obtained in step (d); and
 f) isolating amorphous Lomitapide mesylate.

14. The process as claimed in claim 13, wherein the alcoholic solvent is preferably selected from the group consisting of methanol, ethanol, isopropyl alcohol, tert-butyl alcohol, n-butanol or mixture thereof and more preferably isopropyl alcohol or methanol.

15. The process as claimed in claim 13, wherein the hydrocarbon solvent is preferably selected from the group consisting of cyclohexane, hexane, heptane, n-hexane, n-heptane, toluene and xylene or mixture thereof and more preferably heptane.

16. A pharmaceutical composition comprising a therapeutically effective amount of amorphous Lomitapide mesylate having a Powder X-ray diffractogram as shown in FIG. 3, and at least one pharmaceutically acceptable excipient.

* * * * *